United States Patent [19]

Miyata et al.

[11] Patent Number: 4,843,248
[45] Date of Patent: Jun. 27, 1989

[54] MIXING RATIO SENSOR FOR LIQUID FUEL

[75] Inventors: Shigeru Miyata; Yoshihiro Matsubara, both of Nagoya, Japan

[73] Assignee: NGK Spark Plug Co., Ltd., Nagoya, Japan

[21] Appl. No.: 54,380

[22] Filed: May 26, 1987

[30] Foreign Application Priority Data

Sep. 22, 1986 [JP] Japan ................ 61-145285

[51] Int. Cl.⁴ .................................... G01N 15/06
[52] U.S. Cl. .................................... 250/574; 356/436
[58] Field of Search .............. 250/573, 574, 576, 577; 356/436, 437, 440; 73/29

[56] References Cited

U.S. PATENT DOCUMENTS 4,247,205  1/1981  Typpo ..................... 250/573
4,671,664  6/1987  Fabinski et al. ........ 250/573

Primary Examiner—Edward P. Westin
Assistant Examiner—Khaled Shami
Attorney, Agent, or Firm—Cooper & Dunham

[57] ABSTRACT

A sensor for mixing ratio of liquid fuel comprising, a cylindrical enclosure having both inlet and outlet openings to act as a passage through which a mixing liquid fuel flows. A transparent column concentrically disposed in the enclosure to make the outer surface thereof contact with the liquid fuel, each end of the column is inserted into a ring-shaped wall provided with the inner side of the open end portion of the enclosure. A light emitting diode and a photo diode are provided so as to sandwich the column in the lengthwise direction, so that the light emitted from the former enters the column through its one end and reflects at the boundary of the column and the liquid fuel, and go onto the other end thereof to fall on the latter. A metallic sleeve sealant is provided, one side of which is liquid tightly telescoped into each end of the column, the other side of which is liquid tightly secured to the outer side of the wall to hermetically seal between the liquid fuel and the column.

3 Claims, 1 Drawing Sheet

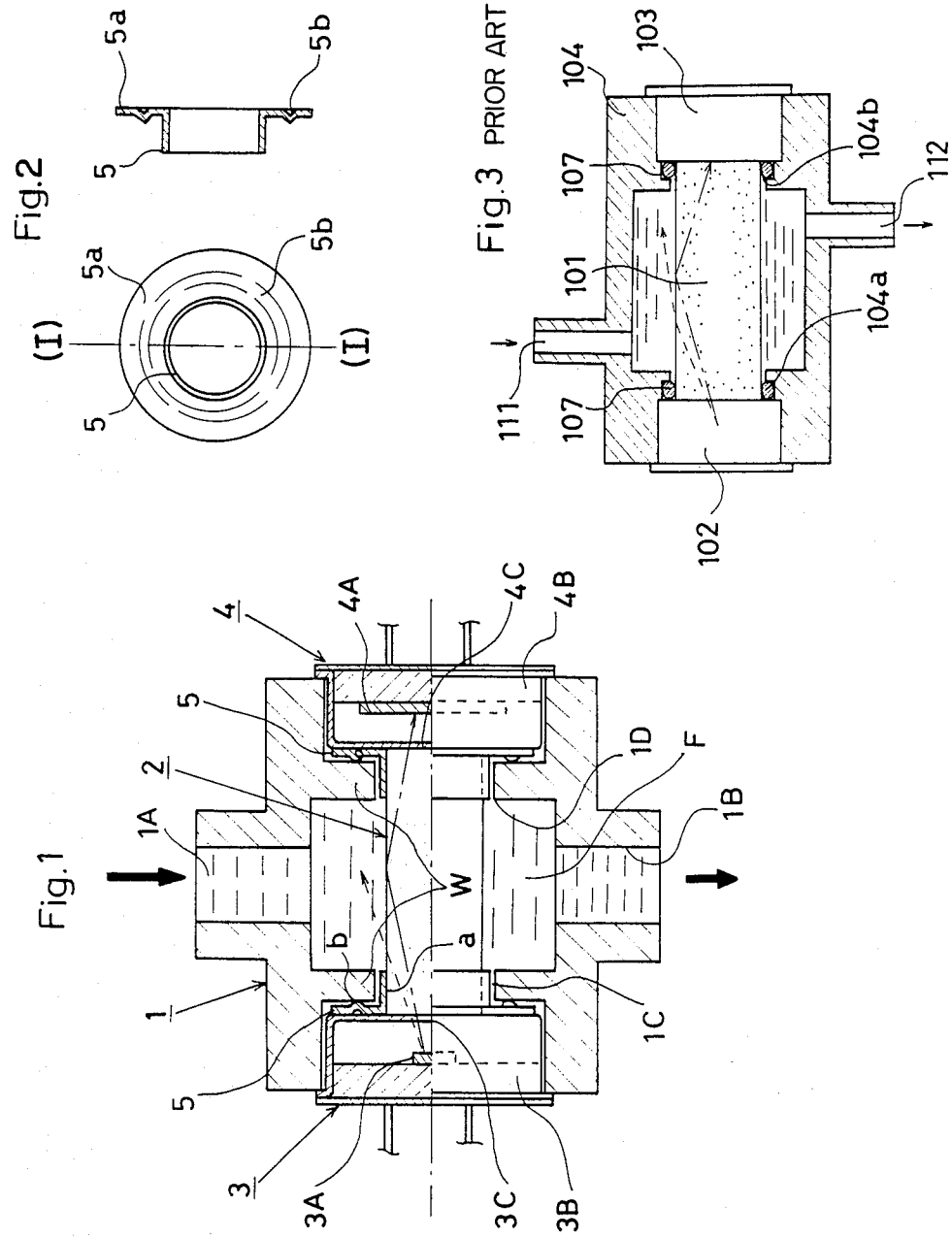

MIXING RATIO SENSOR FOR LIQUID FUEL

BACKGROUND OF THE INVENTION

1. Field of the Invention

This invention relates to a sensor which optically detects a fuel mixing ratio of such as, for example, gasoline and alcohol.

2. Description of the Prior Art

A prior art sensor is shown in FIG. 3 in longitudinal cross section. The sensor has a cylindrical casing 104 having an inlet 111 and an outlet 112, the inner space of which forms a chamber for mixing the liquid fuel. Between ends 104a, 104b, is a transparent glass column 101 interfit with O-rings. Light emitting and photo diodes 102, 103 are provided at both ends of the column 101 in operating relationship with each other.

In this structure, the optically refractivity degree of the glass column relative to the liquid fuel changes depending upon the mixing rate of gasoline and alcohol. Light emitted from the diode 102 is totally reflected at the boundary between the column 101 and the liquid fuel and enters diode 103 to generate an output, the value of which is in accordance with the optical intensity. The output thus generated, indicates the mixing ratio of gasoline and alcohol since the relationship between the output and the mixing ratio of gasoline and alcohol has been previously obtained.

However, the O-ring 107 which is usually made from organic material such as plastics or rubber, is somewhat lacking in chemical and physical stability and deteriorates with surface time, leaving room for improvement in positive and long lasting sealing.

Further, the reflection of the light incident upon the boundary between the column 101 and the mixing liquid fuel, is different in intensity depending upon whether it reflects against the liquid fuel or against the portion in which the O-ring 107 positions.

As a result, the light which reflects at the O-ring 107 and falls on the diode 103, is reduced in intensity, so the linear relationship between the refractive index of the mixing liquid fuel and the output of the diode 103, is lost in some degree.

In order to compensate for the loss of the linear relationship, attention has to be in paid to the liquid-tight configuration and dimensional aspects of column 101.

Therefore, it is an object of this invention to provide a sensor with improved liquid-tight configuration, and which is capable of providing a reliable mixing liquid fuel ratio without affecting the liquid-tight configuration and dimensional aspects of the transparent glass column.

According to the invention, a sensor for mixing ratio of liquid fuel comprising, a cylindrical enclosure having both inlet and outlet opening to act as a passage through which the mixing liquid fuel flows, a transparent column concentrically disposed within into the enclosure so that the outer surface contacts the liquid fuel. Each end of the column is inserted into a ring-shaped wall provided within the inner side of the open end portion of the enclosure. A light emitting diode and a photo diode are provided so as to sandwich or bracket the column in the lenghwise direction, so that the light emitted from the former enters the column through its one end and reflects at the boundary of the column with the liquid fuel, and goes to the other end to fall on the photo diode. Metallic sleeve sealants are provided at each end, one side of each of which is tightly telescoped into each end of the column, the other side of which is liquid tightly secured to the outer side of the wall to form a seal between the liquid fuel and the column.

BRIEF DESCRIPTION OF THE DRAWINGS

FIG. 1 is a longitudinal cross sectional view of a sensor;

FIG. 2 is a plan view of a sleeve sealant, and its longitudinal cross sectional view along the line I—I and;

FIG. 3 is a longitudinal cross sectional view of a prior art counterpart.

PREFERRED EMBODIMENT OF THE INVENTION

A preferred embodiment of the invention is described with reference to FIG. 1. FIG. 1 shows a logitudinal cross sectional view of a sensor according to a preferred embodiment of the invention. In FIG. 1, a cylindrical casing(enclosure) 1 of non-corrosive metal, has inlet and outlet openings (1A), (1B) at its outer peripheral surface through which liquid mixing fuel, such as a mixture of gasoline and alcohol passes.

A transparent column 2 which is made from optical glass or non-corrosive synthetic resin, is concentrically placed at the inner side of the casing 1. and has its outer surface finished to provide minimum roughness both ends of column 2 are inserted into doughnut-shaped walls (1C), (1D). A metallic sleeve sealant 5 made from non-corrosive material is tightly telescoped by means of adhesive into the outer surface (a) of each end of column 2. The sleeve 5 integrally forms a flange portion 5a at one open end, the surface of which has a concentrical ring-shape projection 5b which is liquid tightly secured to the outer surface (b) of the doughnut wall (W) by means of welding, adhesive the like, with the result that the column 2 is supported by the casing 1 by way of the sleeve 5. A light emitting diode 3 is enclosed with its chip (3A) in a metallic case (3B). At one open end of which a window glass (3C) is secured in a side in which the emitted light is directed to one end of the column 2. A photo diode 4 is enclosed at its chip (4A) into a metallic case (4B), to one end of which a window glass (4C) is secured in a manner similar to the diode 3.

It is noted that the sleeve 5 is liquid tightly secured to the outer surface (a) of the column 2 by means of adhesive. Instead of adhesive, the column may be thermally fused at its surface (a) with the sleeve 5 to also make a liquid tight construction.

With the structure thus described, the sleeve 5 is tightly secured to the column 2, while being liquid tightly fixed to the doughnut wall (W) through the ring projection 5b, so the clearance between the column 2 and the inner side of the casing 1 is positively sealed to completely prevent the pressurized liquid fuel from leaking.

In operation, the light emitted from the diode (3A) enters the column 2 through its end portion and reflects at the boundary of the column 2 and the liquid fuel (F) to fall on the photo diode (4A) at the other end of the column 2. The diode (4A) upon being subjected to the light, generates an electrical output in proportion with the amount of the optical flux i.e., refractive index, mixing ratio of the liquid fuel (F). The output thus generated, allows the most appropriate timing of ignition and fuel injection to obtain maximum power of an internal combustion engine. In this instance, the change of the liquid mixing ratio causes to vary the refractive index at the boundary, bringing about the change of optical flux subjected to the photo diode (4A). This change of the ratio varies the output of the diode (4A) to alter the timing of ignition and fuel injection to continuously maintain maximum output power.

It is appreciated that the shape of the sleeve sealant 5 is not necessarily confined to that described in this embodiment, an appropriate change of design may be added, the requirement is that a sleeve sealant is secured at one side to a column, and the other side of a doughnut wall (W) in a liquid tight relationship.

It is also noted that the inner side of the sleeve sealant 5 may be provided with an non-corrosive thin layer by plating or the like to improve the reflection.

Furthermore, with the employment of the sleeve sealant 5, a secondary effect is obtained as follows:

The ring projection 5b which is deformed by means of caulking, allows the doughnut wall (W) to relatively displace against the outer surface (a) of the column 2 without any adverse affect because projection 5b elastically deforms. This prevents undesirable inner strain in the column 2 and the casing 1 due to a difference of thermal expansion therebetween.

What is claimed is:

1. A sensor for mixing ratio of liquid fuel comprising:
   a cylindrical enclosure having both inlet and outlet openings to act as passages through which a mixing liquid flows;
   a transparent column lengthwise disposed within said enclosure to provide an outer surface contact with said mixing liquid fuel, each end of said column being inserted into a ring-shaped wall provided at an open end portion of said enclosure;
   a light emitting diode placed at one end of said column so that light beams emanating from said diode enter into said column, reach the boundary or interface of said column and said mixing liquid fuel, said light beams incident on said boundary or interface at an angle of less than a critical angle being passed to said mixing liquid fuel and said light beams which incident on said boundary or interface at an angle of more than the critical angle are totally reflected back from said boundary or interface;
   a photo diode at other end of said column to receive said light beams totally reflected back from said boundary or interface so as to produce an output, an intensity of which is in accordance with a ratio of said mixing liquid fuel;
   a metallic sealant having a sleeve and a flange provided at one open end of said sleeve, said sleeve being liquid-tight telescoped into each end of said column, while said flange having a circumferential projection liguid-tight secured to an outer side of said wall, thereby securing said mixing liquid fuel against leakage.

2. A sensor as recited in claim 1, in which said sleeve of said sealant is secured to said column by means of thermal fusion or adhesive.

3. A sensor as recited in claim 1, in which said flange of said sealant is secured through said projection by means of welding or adhesive.

* * * * *